United States Patent [19]

Treadwell et al.

[11] 4,312,959

[45] Jan. 26, 1982

[54] NOVEL CATALYST COMPOSITIONS AND METHOD FOR PREPARING POLYURETHANE FOAMS USING SAME

[75] Inventors: Kenneth Treadwell, Rahway; Emily C. Bossert, Westfield, both of N.J.

[73] Assignee: M&T Chemicals Inc., Woodbridge, N.J.

[21] Appl. No.: 234,525

[22] Filed: Feb. 17, 1981

Related U.S. Application Data

[63] Continuation-in-part of Ser. No. 128,848, Mar. 10, 1980, abandoned.

[51] Int. Cl.³ .................. C08G 18/24; C08G 18/14; C08G 18/16
[52] U.S. Cl. .................. 521/107; 252/431 C; 252/431 P; 260/429.7; 260/45.7P; 260/45.7 PH; 260/45.75 K; 521/108
[58] Field of Search .............. 252/431 C, 431 P; 521/108, 107

[56] References Cited

U.S. PATENT DOCUMENTS

| | | | |
|---|---|---|---|
| 3,020,306 | 2/1962 | Birum | 521/108 |
| 3,067,149 | 12/1962 | Dombrow et al. | 521/107 |
| 3,084,177 | 4/1963 | Hostettler et al. | 521/108 |
| 3,281,376 | 10/1966 | Proops | 528/73 |
| 3,505,433 | 4/1970 | Frank et al. | 521/108 |
| 3,620,985 | 11/1971 | Larkin et al. | 521/124 |
| 3,635,821 | 1/1972 | Treadwell | 260/37N |
| 3,641,225 | 2/1972 | Dever et al. | 521/108 |
| 4,021,381 | 5/1977 | Christensen | 521/107 |
| 4,045,378 | 8/1977 | Maxwell | 521/107 |
| 4,048,100 | 9/1977 | Gurgiolo et al. | 521/164 |
| 4,052,346 | 10/1977 | Rudner et al. | 521/112 |
| 4,085,072 | 4/1978 | Russo | 521/108 |
| 4,097,559 | 6/1978 | Papa et al. | 521/107 |

*Primary Examiner*—H. S. Cockeram
*Attorney, Agent, or Firm*—Stanley A. Marcus; Donald G. Marion

[57] ABSTRACT

Polyurethane foams exhibiting excellent thermal and oxidative stability can be prepared using as the polymerization or gel catalyst a composition containing at least one organotin compound containing phosphorus and at least one organotin compound wherein a halogen atom is bonded to tin or phosphorus. The terminal properties of foams obtained using the present catalyst compositions are superior to those exhibited by foams prepared using gel catalyst compositions wherein tin, phosphorus and a halogen are present but the phosphorus and halogen are not in the same molecule as the tin atom. The halogen containing tin compound and the phosphorus-containing tin compound may be identical or different. The recovery properties of the foam can be improved by the presence of a carboxylic acid in the catalyst composition.

46 Claims, No Drawings

NOVEL CATALYST COMPOSITIONS AND METHOD FOR PREPARING POLYURETHANE FOAMS USING SAME

This application is a continuation-in-part of copending application Ser. No. 06/128,848 filed Mar. 10, 1980 and now abandoned.

BACKGROUND OF THE INVENTION

This invention relates to the preparation of polyurethane foams. This invention further relates to the use of certain gel catalyst compositions to prepare polyurethane foams exhibiting high levels of oxidative stability relative to products obtained using conventional organotin catalysts or combinations of these organotin catalysts with compounds containing phosphorus and halogen. Certain of these catalyst compositions are novel and constitute part of this invention.

Flexible polyurethane foams are widely used in the manufacture of furniture, particularly seat cushions, and as packaging material for delicate instruments and other articles that are susceptible to damage during handling and transit. If the foam is incorporated into a piece of furniture or other durable product, the foam must withstand exposure of several years or longer to elevated temperatures, atmospheric oxygen, or both without undergoing significant degradation, as evidenced by a gradual loss of resiliency and structural strength which may ultimately culminate in disintegration of the foam.

It is well known to prepare flexible cellular polyurethanes by reacting polyols containing two or more reactive hydrogen atoms, as determined by the Zerewitinoff method, with polyfunctional isocyanates in the presence of a polymerization or gel catalyst and a blowing agent such as water or a relatively low boiling fluorocarbon. A surfactant is often included in the reaction mixture together with a blowing catalyst to obtain the desired uniformly small cell size within the foam when water is used as the blowing agent. Fillers such as barytes and various additives such as flame retardants can also be present in the formulation employed to prepare the foam.

U.S. Pat. No. 3,620,985 discloses that organotin compounds are effective gel catalysts for cellular polyurethanes. Compounds of the formula $R_aSnX_{4-a}$ wherein R is typically butyl or other alkyl radical containing from 1 to 20 carbon atoms and X is a halogen or other anionic radical are generally less than satisfactory for preparing flexible foams that are exposed to atmospheric oxygen, elevated temperature, i.e. above about 50° C., or both over extended periods of time. Under these conditions the foams may lose resiliency and structural integrity to the extent that they disintegrate when compressed. This is particularly true of those foams derived from polyether-containing polyols that are prepared from propylene oxide. These polyols may also contain ester linkages, (—OOCRCOO—), and end groups derived from ethylene oxide to obtain hydroxyl groups bonded to primary rather than secondary carbon atoms. This susceptibility to degradation can be decreased by employing polyols that contain side chains obtained by the graft polymerization of acrylonitrile, styrene or other vinyl monomer onto poly(propylene oxide), however even these foams undergo a significant decrease in structural strength and become brittle following prolonged exposure to oxygen and/or heat when prepared using conventional organotin catalysts such as dibutyltin dilaurate.

It is known that the resistance of flexible polyurethane foams based on polyether-containing polyols to oxidatively and thermally induced degradation can be improved by employing compounds containing phosphorus and a halogen in combination with an organotin gel catalyst. Catalyst compositions of this type are disclosed in U.S. Pat. Nos. 3,067,149; 4,048,100; 4,052,346 and British Pat. No. 1,003,201. This type of catalyst composition may be suitable for certain applications where resiliency is not a requirement, since foams prepared using these catalyst compositions typically recover only a small fraction of their original height within 30 minutes after being compressed to 10% of their original height for 22 hours at a temperature of 70° C., a conventional method for determining resiliency and dry heat stability of flexible polyurethane foams.

It is possible to improve the dry heat stability without adversely affecting the resiliency of flexible polyurethane foams prepared from polyether-containing polyols using gel catalyst compositions containing an organotin compound, phosphorus and a halogen. Surprisingly it has now been found that if the phosphorus and halogen are both present in the same or different compounds and each compound contains a tetravalent tin atom that is in turn, bonded to at least one hydrocarbyl group, the resultant foam exhibits improved thermal stability relative to foams prepared using an organotin compound as the gel catalyst in the absence of compounds containing phosphorus and a halogen. The resiliency exhibited by the foam following prolonged compression can be further improved by including a mono- or dicarboxylic acid in the catalyst composition.

SUMMARY OF THE INVENTION

This invention provides an improved method for preparing a flexible cellular polyurethane exhibiting improved resiliency and resistance to heat-induced degradation by reacting a polyether-containing polyol containing at least two active hydrogen atoms per molecule, as determined by the Zerewitinoff method, with a polyfunctional isocyanate, the reaction being conducted in the presence of a blowing agent and a catalytically effective amount of a gel catalyst composition containing tin, phosphorus and a halogen. The improvement comprises employing as the gel catalyst (a) a halogenated organotin ester of a phosphorus compound or (b) a halogenated mono- or diorganotin compound and a mono- or diorganotin ester of a phosphorus compound, wherein the halogen atom of (a) is bonded to tin or phosphorus, the halogen in (b) is bonded to tin and the phosphorus compound of (a) and (b) is selected from the group consisting of ortho-phosphoric, meta-phosphoric, pyrophosphoric, thiophosphoric, phosphorous, phosphinic, phosphinous, phosphonous and phosphonic acids, phosphoryl chloride and oligomeric condensation product of (1) phosphonic acid, (2) mixtures containing phosphoric and phosphonic acids or (3) esters of phosphoric and phosphorous acids and alcohols containing from 1 to 20 carbon atoms.

This invention also provides novel gel catatlyst compositions for preparing polyurethane foams exhibiting improved recovery following prolonged compression. These catalyst compositions comprise (1) an organotin compound corresponding to type (a) as previously described or the two organotin compounds corresponding to type (b) and (2) a mono- or dicarboxylic acid containing from 2 to 20 carbon atoms. The acid constitutes up to 90% by weight of the catalyst composition and exhibits the general formula $R^1COOH$ or $HOOCR^2COOH$ wherein $R^1$ represents a monovalent hydrocarbyl group and $R^2$ represents a divalent hydrocarbyl group.

The combination of a halogenated organotin compound and a non-halogenated organotin ester of a phosphorus compound as defined hereinabove is novel, and constitutes one aspect of the present invention.

DETAILED DESCRIPTION OF THE INVENTION

The present gel catalysts are useful for preparing flexible polyurethane foams from substantially all of the known polyether-containing polyols, polyfunctional isocyanates and blowing agents. The concentration of the organotin component of the catalyst is usually from 0.01 to 10%, based on the weight of polyol, preferably from 0.1 to 1%.

Organotin compounds that are suitable for use in the catalyst compositions of this invention are mono- or diorganotin esters of the previously defined class of phosphorus compounds. If the organotin ester does not contain a halogen atom bonded to tin or phosphorus it is employed in combination with mono- or diorganotin compound containing a tin to halogen bond. As used herein the term "halogen" includes chlorine, bromine and iodine.

1. Organotin Compounds Containing Both Phosphorus and a Halogen

Two classes of organotin compounds containing both halogen and phosphorus can be represented by the general formulae

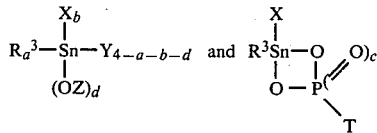

wherein X represents halogen, —OH, —OOCR$^4$, —OR$^4$ or —SR$^5$ wherein R$^4$ is hydrocarbyl and R$^5$ is hydrocarbyl, —R$^6$COOR$^4$ or —R$^6$OOCR$^4$ wherein R$^4$ is as defined above and R$^6$ is alkylene and contains from 2 to 20 carbon atoms; T is halogen or —OR$^9$; Y is

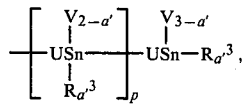

wherein V is —OZ or —X and X is as defined above;

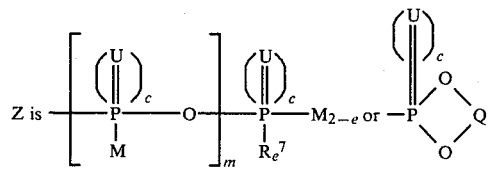

wherein R$^7$ is hydrocarbyl, chloroalkyl, halogen, —OH or —Y', M is —R$^8$, —OR$^9$, —(OR$^{10}$)$_f$OZ' or —Y' R$^8$ is hydrocarbyl, R$^9$ is hydrocarbyl or hydrogen, R$^{10}$ is —CH$_2$CH$_2$— or —CH(CH$_3$)CH$_2$—;

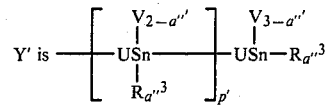

wherein V' is —OZ' or —X, X being defined above;

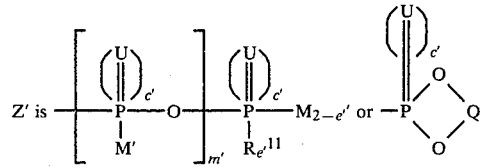

R$^{11}$ is hydrocarbyl, chloroalkyl, halogen or —OH, M' is R$^8$ or —OR$^9$, R$^8$ and R$^9$ are as defined above; U is an oxygen or sulfur atom; R$^3$ is hydrocarbyl or R$^{12}$OOCR$^{10}$—, wherein R$^{10}$ is as defined above and R$^{12}$ is hydrocarbyl, and Q is

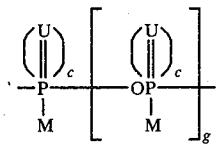

wherein U and M are as defined above; a is 1 or 2; a' is 1 or 2; a'' is 1 or 2; b is 0, 1 or 2 with the proviso that b can only be 0 when the group represented by Y contains a halogen atom bonded to tin or phosphorus; c is 0 or 1; c' is 0 or 1; d is 0, 1 or 2 with the proviso that d can only be 0 when the group represented by Y contains phosphorus; e is 0, 1 or 2; e' is 0, 1 or 2; f is an integer from 1 to 100; g is 0 or an integer from 1 to 6; m is 0 or an integer from 1 to 10; m' is 0 or an integer from 1 to 10; p is 0 or an integer from 1 to 10; and p' is 0 or an integer from 1 to 10.

The term "hydrocarbyl" that is employed in the definition of some substituents, for example R$^4$, R$^5$, R$^7$, R$^8$ and R$^9$ includes alkyl, cycloalkyl, aryl, aralkyl and alkaryl groups. Any alkyl group contains from 1 to 20 carbon atoms.

When any hydrocarbyl is alkyl it can be methyl, ethyl, propyl, butyl, amyl, hexyl, heptyl, octyl, decyl, dodecyl, pentadecyl, hexadecyl, octadecyl or eicosyl. Preferred alkyl groups contain from 1 to 8 carbon atoms. Based on the availability of the organotin halides employed as the starting materials for preparing the organotin compounds employed in the present catalyst compositions R$^3$ in the foregoing general formula is most preferably butyl or octyl when R$^3$ represents an alkyl group. Alternatively R$^3$ can be a carboalkoxyalkyl group, represented by the foregoing formula —R$^{10}$OCOOR$^{12}$. Organotin compounds containing this group can be prepared by reacting metallic tin or a stannous halide with a lower alkyl ester of an ethylenically unsaturated acid such as acrylic or methacrylic acid.

When any hydrocarbyl group is cycloalkyl it can contain from 3 to 8 or more cyclic carbon atoms. Since the most thermodynamically stable cycloalkyl groups are cyclopentyl and cyclohexyl, these are preferred.

The term "aryl" is understood to include groups derived from any of the completely conjugated cyclic hydrocarbons. This group of hydrocarbons includes benzene naphthalene, biphenyl, anthracene and phenanthrene. The preferred aryl group is phenyl, based on the availability of the compounds employed to prepare the organotin compounds, carboxylic acids and esters of phosphorus-containing acids that are, in turn, reacted to prepare the present catalyst compositions.

The terms "aralkyl" and "alkaryl" are understood to include hydrocarbyl groups containing both an alkyl and aryl portion, as previously defined. When the free valence is on the alkyl portion the group is named "aralkyl". Examples of known aralkyl groups include benzyl and β-phenylethyl. Alternatively, the alkyl portion can contain from 3 to 20 carbon atoms and the aryl portion can be any of the previously disclosed aryl groups.

In a narrower embodiment of this invention the hydrocarbyl groups represented by $R^3$, $R^4$, $R^9$ and $R^{12}$ in the foregoing formulae are preferably alkyl, most preferably lower alkyl containing from 1 to 4 carbon atoms. $R^3$ is most preferably butyl, based on the commercial availability of the corresponding organotin halides that are employed as starting materials to prepare the organotin compounds of the invention. Alternatively $R^3$ can be $R^{12}OOCCH_2CH_2$— where $R^{12}$ is preferably lower alkyl, most preferably ethyl.

Preferred substituents represented by the letters T, M, $R^{10}$ and X in the foregoing formulae are as follows:
T halogen or alkoxy containing from 1 to 8 carbon atoms
M —$R^8$, —$OR^9$ or —Y', most preferably alkyl, alkoxy or hydroxyl
$R^{10}$ —$CH_2CH_2$—
X halogen, most preferably chlorine
In the foregoing formulae a is preferably 2, b is 1 or 2, c is 1, d is 0 or 1, e is 0 and m is 0.

A preferred group of organotin compounds containing both phosphorus and halogen can be represented by the general formula

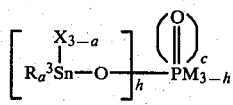

wherein
$R^3$ is alkyl, cycloalkyl, phenylalkyl or alkylphenyl, wherein any alkyl group or the alkyl portion of any phenylalkyl or alkyl phenyl group contains from 1 to 20 carbon atoms, or
$R^3$ is $R^{12}OOCR^{10}$— wherein
$R^{10}$ is —$CH(CH_3)CH_2$— and
$R^{12}$ is alkyl and contains from 1 to 20 carbon atoms;
M is selected from the same group as $R^3$, or is —$OR^9$ wherein $R^9$ is hydrogen or is alkyl, cycloalkyl, phenyl, alkylphenyl or phenylalkyl wherein any alkyl group or the alkyl portion of any alkylphenyl or phenylalkyl group contains from 1 to 20 carbon atoms;
X is chlorine, bromine or iodine;
a is 1 or 2;
c is 0 or 1, and
h is 1 or 2.

When the substituent represented by X in the foregoing general formula is not halogen it can be hydroxyl, carboxy(—$OOCR^4$), hydrocarbyloxy (—$OR^4$), mercapto (—$SR^5$) or the residue remaining following removal of the hydrogen from the sulfur atom of a mercaptan, mercaptoacid ester or mercaptoalkanol ester.

The monovalent hydrocarbyl portion of any of the foregoing groups contains from 1 to 20 carbon atoms. Preferably the hydrocarbyl group is alkyl and contains from 1 to 12 carbon atoms. When —$SR^5$ represents a residue of a mercapto acid ester the mercaptoacid preferably contains from 2 to 8 carbon atoms and is most preferably mercaptoacetic or mercaptopropionic acid. When —$SR^5$ represents the residue of a mercaptoalkanol ester the mercaptoalkanol preferably contains from 2 to 8 carbon atoms and is most preferably mercaptoethanol or mercaptopropanol.

Several organotin esters of phosphorus-containing acids and organic esters thereof are reported in the chemical literature. Compounds containing a single tin atom are prepared by reacting an organotin oxide or hydroxide with an organic ester of the desired phosphorus-containing acid under conditions conventionally employed for transesterification reactions and in the presence of a liquid hydrocarbon that forms an azeotropic mixture with the alcohol formed as a by-product of the transeterification reaction. Alternatively, the unesterified acid can be used or the desired organotin halide can be reacted with the sodium salt of the phosphorus-containing acid or a partial ester thereof.

If the final compound contains a fluorine, chlorine, bromine or iodine atom bonded to tin, the corresponding organohydroxyhalostannane or bis(dihydrocarbylhalo)distannoxane can be employed as the organotin reactant. An example of the former class of compounds is butylchlorodihydroxystannane $C_4H_9SnCl(OH)_2$. This class of compounds is disclosed in U.S. Pat. No. 3,758,536, the pertinent sections of which are hereby incorporated by reference.

Compounds containing one or more groups represented by Y and Y' in the aforementioned structural formula can be prepared using a reaction product of an organotin halide with a diorganotin oxide or organostannoic anhydride when U is oxygen. When U represents sulfur, a diorganotin sulfide or organothiostannoic anhydride is employed. The molar ratio of organotin halide to the oxygen- or sulfurcontaining compound is selected to achieve the desired value of p and p' in the foregoing formulae. Organotin compounds containing a plurality of tin atoms joined by sulfur or oxygen are well known in the chemical literature, and a detailed discussion concerning the preparation of these types of compound in the present specification would be repetitious. The following reactions are typical, wherein Bu represents n—$C_4H_9$—.

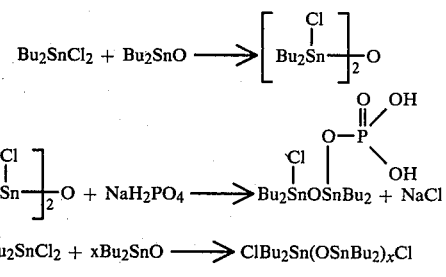

Compounds of the general formula $ClBu_2Sn(OSnBu_2)_xCl$ can exist in linear form as shown. Alternatively these compounds can form cyclic structures wherein the ring contains a plurality of

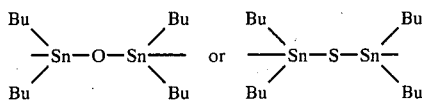

bonds and from 5 to 10 or more atoms. Cyclic compounds of this type are discussed in chapter 12 of a text entitled "The Chemistry of Organotin Compounds" by R. C. Poller (Academic Press, New York, 1970).

The organotin halide can be reacted with the phosphorus-containing acid or a partial or complete ester thereof prior to or following reaction of the organotin halide with the organotin compound containing oxygen or sulfur. An example of the former is represented by the reaction

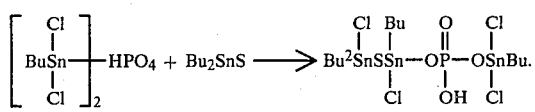

Additional tin atoms can be introduced into the molecule by increasing the molar ratio of the diorganotin sulfide. Alternatively, the corresponding diorganotin oxide can be used in place of the sulfide.

The foregoing reaction also demonstrates that the present compounds may contain both monoorganotin and diorganotin groups.

During preparation of the present compounds an alkali metal salt of the desired phosphorus-containing acid or a partial ester thereof can be reacted with a bis(organohalotin)oxide using an alcohol as the reaction medium. This reaction proceeds relatively rapidly at a temperature from ambient to about 50° C. The advantage of using alcohols is that the reaction product is usually soluble and the sodium halide formed as a by-product precipitates from the reaction mixture. Alternatively, the free phosphorus-containing acid can be reacted with an organotin oxide or an organostannoic anhydride in a liquid hydrocarbon such as toluene that forms an azeotropic mixture with the water formed as a by-product of the reaction. In this instance the reaction is conducted at the boiling point to remove the by-product water as it is formed, thereby providing a driving force for the reaction.

In addition to alcohols and liquid hydrocarbons, the optional liquid carboxylic acid component of the present catalyst composition can be used as the reaction medium for preparing the organotin compounds employed as gel catalysts in accordance with this invention. Under these conditions at least a portion of the carboxylic acid may react with the organotin component of the catalyst composition. It has been found that if the resultant diluted reaction product is employed as a gel catalyst for a flexible polyurethane foam, the thermal stability and resiliency of the foam is superior relative to foams prepared in the absence of the acid.

The phosphorus-containing acids suitable for use in preparing the organotin component of the present catalyst compositions include ortho-phosphoric, meta-phosphoric and pyro-phosphoric acids, thiophosphoric, phosphorus, phosphinic, phosphinous, phosphonous and phosphonic acids. It is known that phosphonic acid will condense with itself or with phosphoric acid under certain conditions to form oligomeric products. These oligomers are subsequently reacted with organotin oxides, organotin halides or mixtures thereof as previously described to form the organotin component of the present catalyst compositions.

The accompanying examples disclose procedures for preparing the various classes of catalysts that are useful in accordance with the present method.

Examples of specific organotin compounds containing both phosphorus and halogen that are within the scope of this invention are represented by the formulae

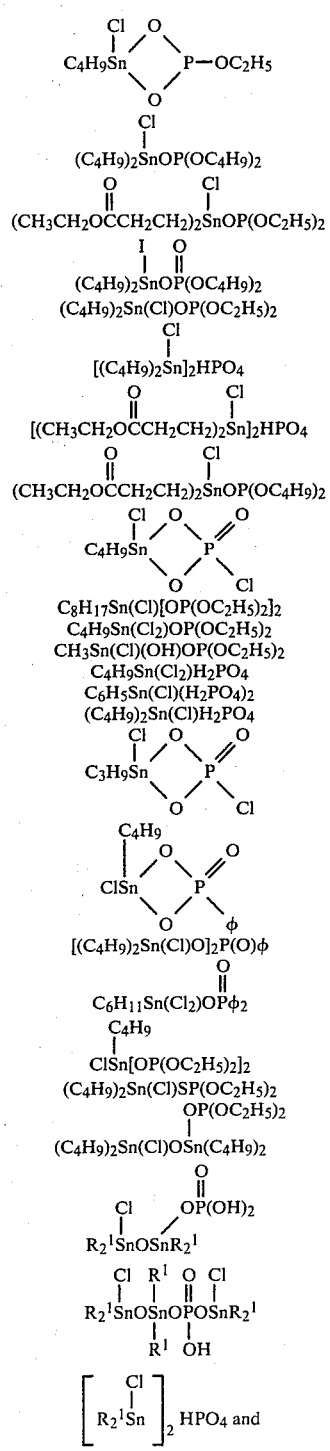

-continued $$\underset{\underset{\text{OH}}{|}}{R_2{}^1Sn}-\overset{\underset{\text{SCH}_2\text{COOR}^{11}}{|}}{S}-Sn(R^1)_2O\overset{\underset{\text{O}}{\|}}{P}O\overset{\text{Cl}}{\underset{|}{}}SnR_2{}^1 \text{ wherein } R^{11} \text{ is hydrocarbyl.}$$

The last of the aforementioned compounds can be prepared by replacing a chlorine atom with a mercaptoester group using equimolar amounts of ester and organotin compound.

When the hydrocarbon group bonded to tin in the foregoing formulae is specified it is often shown as butyl. It should be obvious, however, that compounds containing other hydrocarbon groups, e.g. methyl, octyl, phenyl and cyclohexyl, would be equally suitable for use in the present catalyst compositions.

2. Catalyst Compositions Containing a Halogen and Phosphorus in Different Organotin compounds As previously disclosed, if the organotin ester of the phosphorus compound does not contain a tin-halogen or phosphorus-halogen bond, a mono- or diorganotin compound containing a tin-halogen bond must be present in the catalyst composition. In preferred compositions the relative amounts of halogen-containing and phosphorus-containing organotin compounds are such that the molar ratio of tin to phosphorus is from 0.045 to 23, the molar ratio of tin to halogen (bonded to tin) is from 0.5 to 23 and the molar ratio of phosphorus to halogen (bonded to tin) is from 0.5 to 22. The halogen-containing organo-tin compound can be represented by the general formula $R_a{}^3SnX_{4-a}$ wherein $R^3$ is hydrocarbyl or $R^2OOCR^{10}$—, $R^{10}$ and $R^{12}$ having previously been defined, X is a halogen and a is 1 or 2. $R^3$ is preferably lower alkyl, most preferably butyl, and X is preferably chlorine.

Preferred phosphorus-containing organotin compounds can be represented by the general formula

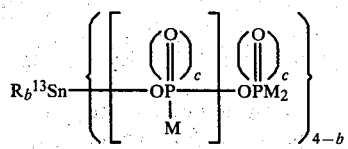

where $R^{13}$ is hydrocarbyl or $R^{14}OOCR^{15}$—, where $R^{14}$ and $R^{15}$ are selected from the same group as $R^{12}$ and $R^{10}$, respectively.

Representative phosphorus-containing organotin compounds include dibutyltin phosphate, dibutyltin phosphite and dibutyltin bis(diethyl phosphate). Representative of the organotin halides that can be employed in the catalyst compositions of this invention include dibutyltin dichloride, dioctyltin dichloride, dibutyltin dibromide and methyltin trichloride and butyltin trichloride.

An example of a preferred catalyst composition containing two organotin compounds is dibutyltin dichloride and dibutyltin phosphate. The latter compound can be represented by the formula

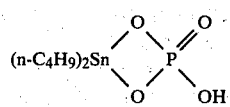

3. The Optional Carboxylic Acids and Diluents

The optional component of the present catalyst compositions is a mono- or dicarboxylic acid containing from 2 to 20 carbon atoms. Acids containing from 6 to 12 atoms are preferred due to the improvement in recovery properties imparted to polyurethane foams by catalyst compositions containing these acids.

Representative monocarboxylic acids that can be employed in the present catalyst compositions include acetic, propionic, butyric, iso-butyric, hexanoic, the isomeric octanoic acids, including 2-ethylhexanoic acid, decanoic, dodecanoic, myristic, heptadecanoic and eicosanoic acids. Useful dicarboxylic acids include succinic, adipic, maleic and sebacic acids.

The mono- or dicarboxylic acid constitutes up to 90% by weight, preferably from 10 to 90% by weight of the present catalyst compositions. Data in the accompanying examples demonstrate that the ability of polyurethane foams to recover their original height following prolonged compression is significantly improved when a carboxylic acid such as 2-ethylhexanoic acid is employed in combination with the aforementioned class of organotin compounds containing phosphorus and an active halogen.

In addition to the aforementioned organotin compounds and carboxylic acid the present catalyst compositions may contain one or more diluents which are solvents for all components of the catalyst composition at the desired concentration levels. The diluent may be inert or it may be reactive with the polyfunctional isocyanate employed to prepare polyurethane foams. A preferred class of diluents are the oligomeric alkylene glycols such as dipropylene glycol.

Since the concentration of the present gel catalyst compositions required to prepare a polyurethane foams is relatively low, i.e. 0.01 to 1% of organotin compounds, based on the weight of polyol, it may be desirable to combine the catalyst composition with one or more of the aforementioned diluents before adding the composition to the reaction mixture employed to prepare a polyurethane foam.

4. Preparation of Flexible Polyurethane Foams

Flexible polyurethane foams of improved oxidative stability are prepared by reacting a polyfunctional isocyanate with a polyol containing ester (—C—O—C) or a combination of ether and ester

groups and two or more reactive hydrogen atoms as determined by the Zerewitinoff method. In accordance with the present method, this reaction is catalyzed by one of the catalyst compositions of this invention. This reaction is usually exothermic and occurs concurrently with gas evolution, resulting in formation of a cellular structure. The gas-evolving or blowing agent can be water, which reacts with excess polyfunctional isocyanate to yield carbon dioxide. Water can be used in combination with a volatile liquid fluorocarbon such as trichlorofluoromethane or dichlorofluoromethane. When water is present as a blowing agent the reaction mixture may also contain a blowing catalyst to coordinate the rates of the foaming and polymerization reactions, thereby retaining structural integrity and achieving the desired uniformly small cell size within the foam. Tertiary amines such as bis(N,N-dimethylaminoethyl)ether and triethylene diamine are preferred blowing catalysts. One tenth to five tenths of one part by weight of blowing catalyst is usually employed for every one hundred parts of polyol. Silicon compounds, particularly reaction products of silanes with 1,2-olefin oxides, are often included as cell modifying agents, commonly referred to as surfactants.

If one or more amines are employed as blowing catalysts, these will also catalyze the reactions between the polyfunctional isocyanate and polyol. The use of amines as gel catalysts is well known in the prior art, however, amines are often less than satisfactory due to their low catalytic activity. In the past it was necessary to employ a prepolymer in order to attain the desired molecular weight while avoiding unduly long rise times.

The polyfunctional isocyanates used to prepare polyurethanes using the present gel catalysts include both polyisocyanates and polyisothiocyanates. While the invention is described with specific references to the reaction of certain diisocyanates, it is generally applicable to the reaction of any compound containing two or more —N=C=G radicals wherein G is oxygen or sulfur. Compounds within this generic definition include polyisocyanates and polyisothiocyanates of the formula R (NCG)$_x$ in which x is 2 or more. R can be alkylene, substituted arylene or other divalent hydrocarbon radical that may optionally contain one or more aryl-NCG bonds and one or more alkyl-NCG bonds.

Although a variety of organic polyisocyanates containing 3 or more isocyanate radicals per molecule can be used in the practice of this invention, diisocyanates are usually preferred in flexible foam formulations. Suitable isocyanates include alkylene diisocyanates such as hexamethylene diisocyanate, and decamethylene diisocyanate, the isomeric toluene diisocyanates and naphthalene diisocyanates, 4,4'-diphenylmethane diisocyanate and mixtures of two or more of the foregoing diisocyanates. Triisocyanates obtained by reacting 3 moles of an arylene diisocyanate for each mole of a triol, e.g., the products formed from 3 moles of tolylene diisocyanate and 1 mole of hexane triol may also be present in the reaction mixture. A preferred polyisocyanate is a mixture containing 80% by weight of the 2,4-isomer and 20 percent of the 2,6-isomer of toluene diisocyanate. Other suitable polyfunctional isocyanates include hexamethylene diisocyanate, xylylene diisocyanate, 1-methyl-2,4-diisocyanates, diphenylmethane-4,4'-diisocyanate, naphthalene-1,5-diisocyanate, triphenylmethane-4,4',4''-triisocyanate and xylene-α,α'-diisothiocyanate. Oligomeric and polymeric isocyanates of the general formulae (R NCG)$_x$ and [R (NCG)$_x$]$_y$ in which x and y are between 2 and 10, are also useful in the present method, as are compounds of the general formula M (NCG)$_x$ wherein x is 2 or more and M is a difunctional or polyfunctional atom or group. An example of this type is polymethylene polyphenylisocyanate.

Suitable polyether-type polyols include polyalkylene glycols such as polyethylene glycols and polypropylene glycols. The molecular weight of these compounds is preferably between about 200 and 5000.

As previously disclosed, polyols containing both ether and ester groups within the molecule are suitable for preparing polyurethane foams using the catalysts of this invention.

The preparation of polyurethane foams can be accomplished by forming a prepolymer, i.e. prereacting molar equivalents of a hydroxyl-terminated polyol and isocyanate in the absence of water and thereafter producing a foam by the addition of excess isocyanate, water and optionally other blowing agents and one of the present gel catalysts. Alternatively, foams may be produced by the "one-shot" method in which all of the reactants and catalysts are mixed together and allowed to react in the presence of water or other blowing agent.

The polyfunctional isocyanate is typically present in an amount of 5 to 300 percent, preferably from 30 to 50 percent by weight of the polyol. Water may optionally be present as a blowing agent to react with excess isocyanate and generate sufficient carbon dioxide to produce a foam of the desired density. The amount of water is between 1 and 10 percent, preferably between 2 and 5 percent, based upon the weight of the polyol.

The amount of isocyanate used can be in excess of the stoichiometric amount required to react with the active hydrogen atoms present in the polyol and any water present, thereby forming allophanate

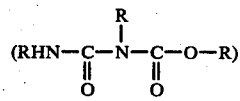

and biuret

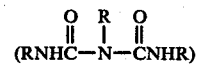

linkages in the polymer chains. Depending upon the desired density of the urethane foam and the amount of crosslinking desired, the ratio of equivalent weights of isocyanate groups to moles of active hydrogen atom present in the polyol and any water present should be from 0.8 to 1.2, respectively, preferably between 0.9 and 1.1.

The concentration of gel catalyst is from 0.13 to 10 parts by weight per 100 parts of polyol. Preferably the gel catalyst is present in an amount corresponding to between 0.1 to 1.0 part by weight per 100 parts of polyol. If a blowing catalyst is employed, it is present at a concentration of from 0.01 to 10 parts per 100 parts of polyol.

The optimum concentration of gel catalyst is dependent upon the particular formulation employed to prepare a polyurethane foam. For example, increasing the amount of tertiary amine in a formulation or adding a conventional gel catalyst such as stannous octoate will often significantly reduce the amount of the present catalysts required to produce an acceptable foam. The concentration range of the present gel catalysts that is optimum for a given formulation is readily determinable by routine experimentation.

The formulation employed to prepare polyurethane foams using the gel catalyst of this invention may contain various additives conventionally incorporated into flexible polyurethane foams. These additives include fillers such as barytes and calcium carbonate, flame retarding agents such as antimony oxide, phosphorous compounds such as triphenylphosphine oxide and halogen-containing polymers such as polyvinyl chloride.

The following examples demonstrate the oxidative stability and excellent recovery properties that distinguish flexible foams prepared using the present gel catalysts from those obtained using organotin compounds alone or in combination with a halogen compound and a phosphorus compound. All parts and percentages are by weight unless otherwise specified.

EXAMPLE 1

Preparation of Dibutylchlorotin Diethyl Phosphite $$2Na + 2HOP(OEt)_2 \longrightarrow 2NaOP(OEt)_2 + H_2$$

$$Bu_2SnCl_2 + NaOP(OEt)_2 \longrightarrow \overset{Cl}{\underset{|}{Bu_2SnOP(OEt)_2}} + NaCl$$

Sodium diethyl phosphite was prepared by stirring under a nitrogen atmosphere 9.2 g (0.4 AU) sodium and 55.2 g (0.4 mole) diethyl hydrogen phosphite in 150 cc of tetrahydrofuran while maintaining the temperature of the reaction mixture below 41° C. The resultant product was then added dropwise to a solution containing 122 g (0.4 mole) of dibutyltin dichloride and 100 cc tetrahydrofuran. The addition was carried out under a nitrogen atmosphere and the temperature of the reaction mixture was first maintained at 40° C. for 2 hours and then at ambient temperature for 3 hours. The reaction mixture was then filtered and the solvent removed by evaporation under reduced pressure. The residual material was again filtered and the diethyl hydrogen phosphite removed by heating the filtrate at 80° C. under reduced pressure until no additional distillate could be collected. The residue weighed 134 g and was found to contain 29.08% tin, 9.49% chlorine and 6.89% phosphorus. The calculated values for these elements in the expected product are 29.28%, 8.76% and 7.64%, respectively.

EXAMPLE 2

Preparation of Bis(dibutylchlorotin) Phosphate

A glass reactor was charged with 91.1 g (0.3 mole) dibutyltin dichloride, 200 cc n-butanol, 50 cc water and 27.3 g (0.15 mole) dibasic sodium phosphate dihydrate. The resultant mixture was heated under a nitrogen atmosphere and the water removed by azeotropic distillation until the vapor temperature reached 117° C. The reaction mixture was then filtered and the liquid phase was concentrated under reduced pressure. The liquid residue solidified upon standing and weighed 83 g. The product was found to contain 34.60% tin, 11.18% chlorine and 4.42% phosphorus. The calculated values for these elements in the expected product are 37.53% tin, 11.21% chlorine and 4.90% phosphorus.

EXAMPLE 3

Preparation of Di[bis($\beta$-carboethoxyethyl)chlorotin]- Phosphate

A glass reactor was charged with (1) a solution that had been prepared by dissolving 39.2 g (0.1 mole) bis($\beta$-carboethoxyethyl)tin dichloride in 150 cc of toluene, and (2) 7.1 g (0.05 mole) dibasic sodium phosphate. The resultant mixture was stirred and heated to the boiling point (109° C.) for 2 hours, then cooled to 90° C. and filtered. The filtrate was then concentrated under reduced pressure to yield 35 g of a liquid product, di[bis($\beta$-carboethoxyethyl)chlorotin]phosphate, which was found to contain 23.22% tin, 8.96% chlorine and 5.77% phosphorus.

EXAMPLE 4

Preparation of Butychlorotin Cyclic 0,0'-monoethyl Phosphite

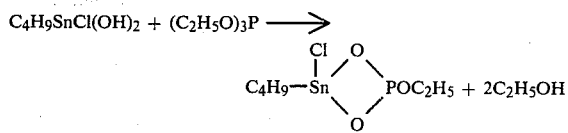

A glass reactor was charged with 73.6 g (0.3 mole) butylchlorotin dihydroxide, 49.9 g (0.3 mole) triethyl phosphite and 225 cc toluene. The resultant mixture was stirred and heated to 95° C. and the by-product ethanol was removed using azeotropic distillation. The reaction mixture was then heated to the boiling point for one hour, after which the mixture was filtered and the filtrate concentrated under reduced pressure. The residue weighed 102 g and was found to contain 32.83% tin, 8.50% phosphorus and 8.83% chlorine. The calculated values for the expected product are 33.66% tin, 8.77% phosphorus and 10.06% chlorine.

EXAMPLE 5

Preparation of Dibutylchlorotin Dibutyl Phosphite $$(C_4H_9)_2SnCl_2 + NaOP(OC_4H_9)_2 \longrightarrow$$

$$\overset{Cl}{\underset{|}{(C_4H_9)_2SnOP(OC_4H_9)_2}} + NaCl$$

The aforementioned compound was prepared by the gradual addition, under a nitrogen atmosphere, of 4.8 g (0.2 mole) sodium hydride to 38.8 g (0.2 mole) dibutyl hydrogen phosphite which had previously been dissolved in 50 cc of tetrahydrofuran. The resultant mixture was heated for 4 hours at 65° C., after which it was cooled to ambient temperature and added dropwise to 60.7 g (0.2 mole) dibutyltin dichloride which had previously been dissolved in 100 cc of tetrahydrofuran. The resultant mixture was then heated under a nitrogen atmosphere for 3 hours at 65° C., after which it was filtered and the filtrate concentrated under reduced pressure to yield 68 g of a clear amber liquid. The liquid was found to contain 27.87% tin, 7.17% chlorine and 4.89% phosphorus. The calculated values for the expected product are 25.73% tin, 7.69% chlorine and 6.72% phosphorus.

EXAMPLE 6

Preparation of Bis($\beta$-carboethoxyethyl)chlorotin Diethyl Phosphite $$Na + HOP(OC_2H_5)_2 \longrightarrow NaOP(OC_2H_5)_2 + H_2$$

$$(CH_3CH_2O\overset{O}{\overset{\|}{C}}CH_2CH_2)_2SnCl_2 + NaOP(OC_2H_5)_2 \longrightarrow$$

$$(CH_3CH_2O\overset{O}{\overset{\|}{C}}CH_2CH_2)_2\overset{Cl}{\underset{|}{Sn}}OP(OC_2H_5)_2 + NaCl$$

A glass reactor equipped with a mechanically driven stirrer, condenser and nitrogen inlet was charged with 4.6 g sodium. Diethyl hydrogen phosphate, 27.6 g (0.2 mole), dissolved in 50 cc tetrahydrofuran was added slowly while the temperature was maintained below 30° C. The reaction mixture was stirred at room temperature for 3 hours. The resultant sodium diethyl phosphite was added dropwise to 78.4 g (0.2 mole) bis($\beta$-carboethoxyethyl)tin dichloride in 150 cc tetrahydrofuran. An exothermic reaction occurred. The reaction mixture was stirred at ambient temperature for 3 hours and then filtered. Residual solvent was removed under reduced pressure. The the liquid residue weighed 81 g.

|      | Calculated | By Analysis |
| ---- | ---------- | ----------- |
| % Sn | 24.06      | 22.84       |
| % P  | 6.28       | 5.83        |
| % Cl | 7.19       | 9.06        |

EXAMPLE 7

Preparation of Bis($\beta$-carboethoxyethyl)chlorotin Dibutyl Phosphite

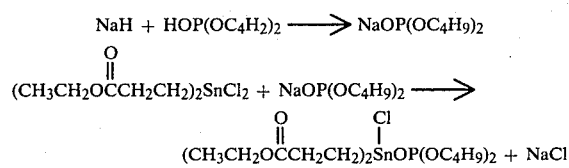

Sodium dibutyl phosphite was prepared by the gradual addition at room temperature of 19.4 g (0.1 mole) dibutyl hydrogen phosphite to a solution containing 2.4 g (0.1 mole) sodium hydride and 50 cc tetrahydrofuran. The mixture was stirred at room temperature for 6 hours and 39.2 g (0.1 mole) bis($\beta$-carboethoxyethyltin) dichloride dissolved in 50 cc of tetrahydrofuran were added. The temperature spontaneously increased to 60° C. Following completion of the addition the reaction mixture was heated at 65° C. for 2 hours. The mixture was filtered and the filtrate was then concentrated under reduced pressure. 41 g of liquid product was obtained.

|      | Calculated | By Analysis |
| ---- | ---------- | ----------- |
| % Sn | 21.61      | 21.00       |
| % Cl | 6.46       | 6.65        |
| % P  | 5.64       | 5.55        |

EXAMPLE 8

Preparation of Butylchlorotin Cyclic-O,O'-chlorophosphordate

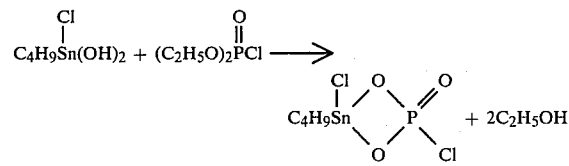

A glass reactor equipped with a mechanically driven stirrer, condenser, thermometer, nitrogen inlet and Dean Stark trap was charged with 73.6 g (0.3 mole) butylchlorotin dihydroxide, 51.8 g (0.3 mole) diethyl chlorophosphate and 200 cc of toluene. The mixture was heated to 95° C. to remove ethanol by azeotropic distillation. After all the ethanol was removed, the reaction mixture was concentrated under reduced pressure to yield 94 g of a liquid which contained the desired product.

EXAMPLE 9

Preparation of Dibutyliodotin Dibutyl Phosphate

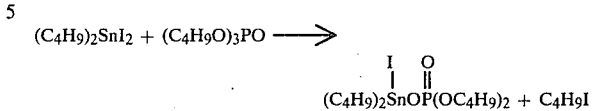

A glass reactor equipped with a condenser, stirrer and nitrogen inlet was charged with 43.5 g dibutyltin diiodide and 19.5 g tributyl phosphate. The resultant mixture was heated to 125°–195° C. When 17.8 g of 1-iodobutane were collected, heating was discontinued and the reaction mixture was allowed to cool to ambient temperature. 44 g of a white solid product was obtained.

EXAMPLE 10

Preparation of Flexible Polyurethane Foams

The compounds described in the preceeding nine examples were employed as gel catalysts for flexible polyurethane foams using the following formulation:

| Ingredient | Parts (by weight) |
| --- | --- |
| Polyol[1] | 100 |
| Water | 3.5 |
| Poly(oxyethylene oxypropylene) siloxane | 1.0 |
| Blowing catalyst[2] | 0.45 |
| Gel catalyst | as specified |
| Toluene diisocyanate[3] | 45.5 |

[1] An ethylene oxide-propylene oxide copolymer available as Niax ® 16-56 from the Union Carbide Corporation.
[2] A mixture containing 0.15 part of a commercially available tertiary amine blowing catalyst (Polycat ®-77, distributed by Abbott Laboratories) and 0.30 part of triethylenediamine (as a 33% solution in dipropylene glycol).
[3] Isocyanate index = 105

The reagents were blended for five seconds using a high speed mixer and then poured into a one liter-capacity polyethylene-lined paper cup and allowed to rise. Each of the resultant cylindrical foam samples was cut in half lengthwise and one of the halves was tested for oxidative and thermal stability in accordance with the procedure set forth in the American Society for Testing and Materials (ASTM) Test Method D-1564-71 (suffix A). The sample to be tested was placed in a circulating air oven at a temperature of 140° C. for 22 hours, then withdrawn from the oven and allowed to cool for between 10 and 15 minutes. A portion of the flat surface of each sample was depressed to the maximum extent and the pressure released almost immediately. Samples that were sufficiently resilient to recover their original shape without any visible damage were considered to have passed the test and all others were considered failures.

The procedure employed to determine the 90% compression set value is described in the aforementioned ASTM test method, and consists of compressing a foam sample to 10% of its original height for 22 hours at a temperature of 70° C. The height of the foam sample is measured prior to compression and thirty minutes following release of compression. The 90% compression set value is calculated using the formula $$90\% \text{ compression set} = (t_o - t_f / t_o - t_s) \times 100$$

In the foregoing formula $t_o$ is the height of the foam sample prior to compression, $t_f$ is the height of the sample measured 30 minutes following the release of compression and $t_s$ is the height of the spacer bar employed in the test procedure described in the aforementioned ASTM method.

Polyurethane foams employed in seat cushions and mattresses should exhibit 90% compression set loss values of less than about 15%. All of the present catalyst evaluated produced foams that were within this range. By comparison, foams prepared using several prior art catalyst compositions wherein the tin, phosphorus and halogen are distributed among two or three compounds exhibited 90% compression set values considerably above 15% and as high as 90%. These foams would not be suitable for use in seat cushions or mattresses.

The cream time, rise time, dry heat test results (pass or fail) and the 90% compression set values for three of the catalysts disclosed in the preceeding examples are summarized in the following table together with the values obtained using stannous octoate as a control catalyst.

| Parts of dibutylchlorotin diethyl phosphite | 0.13 Part | 0.25 Part | 0.37 Part |
|---|---|---|---|
| Cream time, sec. | 10 | 11 | 11 |
| Rise time, sec. | 82 | 76 | 78 |
| Dry heat test | Pass | Pass | Pass |
| 90% Compression set, % loss | 8 | 8 | 12 |
| Parts of bis(dibutylchlorotin) phosphate | 0.8 Part | 0.4 Part | |
| Cream time, sec. | 12 | 13 | |
| Rise time, sec. | 79 | 90 | |
| Dry heat test | Pass | Pass | |
| 90% Compression set, % loss | 12 | 8 | |
| Parts of di[bis(β-carboethoxyethyl)chlorotin]phosphate | | | 0.6 Part |
| Cream time, sec. | | | 12 |
| Rise time, sec. | | | 82 |
| Dry heat test | | | Pass |
| 90% Compression set, % loss | | | 8 |
| Parts of Stannous octoate | | | 0.3 Part |
| Cream time, sec. | | | 10 |
| Rise time, sec. | | | 81 |
| Dry heat test | | | Pass |
| 90% Compression set, % loss | | | 9 |

The combination of dibutyltin dilaurate and tris(2-chloroethyl) phosphate is exemplified in U.S. Pat. No. 3,087,149. The foam properties achieved using this prior art catalyst composition with one formulation identical to the one described in the preceding specification and a second one described in the aforementioned U.S. Pat. No. 3,087,149 are summarized below.

The polyol disclosed in the aforementioned patent was replaced by the polyol employed in the formulation described in the preceding specification. The resultant foam passed the dry heat stability test, however, the 90% compression set value was 58%. When the same prior art catalyst components were employed in the formulation described in the present specification the foam properties were as follows.

| Parts of tris-(2-chloroethyl) phosphate | Parts of dibutyltin dilaurate | Cream Time Sec. | Rise Time Sec. | Dry Heat Test | 90% Compression Set (after heating) % loss |
|---|---|---|---|---|---|
| 0 | 0.5 | 9 | 75 | Fail | not determined |
| 1.5 | 0.2 | 10 | 68 | Pass | 77 |
| 1.5 | 0.35 | 9 | 71 | Pass | 36 |
| 2 | 0.5 | 9 | 80 | Pass | 80 |
| 4 | 0.5 | 9 | 67 | | 82 |

EXAMPLE 11 (Control)

This example demonstrates that combinations of an organotin compound and a phosphorus compound which does not contain tin do not provide the desired 90% compression set value of 15% of less. The formulation employed to prepare the foam was identical to that described in the first paragraph of the preceding Example 10.

| A | |
|---|---|
| Tris(2-chloroethyl) phosphate | 0.46 part |
| Dibutyltin bis(isooctyl maleate) | 0.53 part |
| Cream time, sec. | 12 |
| Rise time, sec. | 66 |
| Dry heat test | Pass |
| 90% Compression set, % loss | 91 |
| B | |
| Diethylhydrogen phosphite | 0.20 part |
| Dibutyltin dichloride | 0.45 part |
| Cream time, sec. | 23 |
| Rise time, sec. | 104 |
| Dry heat test | Pass |
| 90% Compression set, % loss | 78 |
| C | |
| Tris(2-chloroethyl) phosphate | 0.29 part |
| Dibutyltin bis(lauryl mercaptide) | 0.34 part |
| Cream time, sec. | 11 |
| Rise time, sec. | 60 |
| Dry heat test | Pass |
| 90% Compression set, % loss | 89 |
| D | |
| Tris(2-chloroethyl) phosphate | 0.135 part |
| Dibutyltin dilaurate | 0.115 part |
| Cream time, sec. | 11 |
| Rise time, sec. | 77 |
| Dry heat test | Pass |
| 90% Compression set, % loss | 92 |
| E | |
| Tris(nonylphenyl) phosphite | 0.54 part |
| Dibutyltin dichloride | 0.24 part |
| Cream time, sec. | 19 |
| Rise time, sec. | 107 |
| Dry heat test | Pass |
| 90% Compression set, % loss | 88 |
| F | |
| Triisodecyl phosphite | 0.32 part |
| Dibutyltin dichloride | 0.20 part |
| Cream time, sec. | 15 |
| Rise time, sec. | 99 |
| Dry heat test | Pass |
| 90% Compression set, % loss | 88 |

EXAMPLE 12

This example demonstrates that foams prepared using a number of the present catalysts exhibit acceptable levels of dry heat stability and resiliency, the latter having been determined using the value for 25% indent load deflection (ILD) measured using ASTM test method D-1564-71 (suffix A). The catalysts are identified using the number of the example in the preceeding specification that discloses the preparation of the compound.

| Compound of Example | Catalyst level, parts | Cream time, sec. | Rise time, sec. | Dry heat test | 25% ILD lb./50in$^2$ |
|---|---|---|---|---|---|
| Control* | 0.3 | 10 | 80 | Pass | 25 |
| 1 | 0.13 | 10 | 82 | Pass | — |

| Compound of Example | Catalyst level, parts | Cream time, sec. | Rise time, sec. | Dry heat test | 25% ILD lb./50in² |
|---|---|---|---|---|---|
| 2 | 0.40 | 13 | 90 | Pass | 14 |
| 3 | 0.60 | 12 | 82 | Pass | 22 |
| 4 | 0.20 | 13 | 86 | Pass | 20 |
| 5 | 0.35 | 13 | 76 | Pass | 25 |
| 6 | 0.20 | 12 | 67 | Pass | 22 |
| 7 | 0.35 | 10 | 66 | Pass | 17 |
| 8 | 0.20 | 17 | 124 | Pass | — |

*Stannous octoate

The formulation employed to prepare the foams was identical to the one described in the first paragraph of the preceding Example 10.

EXAMPLE 13

Preparation of Dibutylchlorophosphatostannoxane

A mixture containing 30.4 g (0.1 mole) of dibutyltin dichloride, 49.8 g (0.2 mole) of dibutyltin oxide and 250 cc of toluene was heated with stirring until a clear solution formed. A 11.5 g (0.1 mole) portion of an 85% aqueous solution of ortho-phosphoric acid was then added to the reactor and the resultant mixture was heated at the boiling point for two hours, during which time the water formed as a by-product was removed using a Dean-Stark receiver. The liquid phase of the reaction mixture was evaporated under reduced pressure and the resultant solid was dried in an oven at a temperature of 75° C. and under a partial vacuum. The dried solid weighed 77.4 g and was found to contain 39.4% tin, 3.15% phosphorus and 7.61% chlorine. The calculated values for the expected product, which can be expressed by the empirical formula $Sn_3C_{24}H_{55}Cl_2PO_5$ are 40.4% tin, 3.52% phosphorus and 8.05% chlorine. This product was dissolved in 2-ethylhexoic acid to form a 33% by weight solution which was subsequently evaluted as a gel catalyst for a polyurethane foam.

EXAMPLE 14

This example demonstrates the preparation of a reaction product of bis(dibutylchlorotin)phosphate, dibutyltin sulfide and 2-ethylhexanoic acid.

A mixture containing 2.65 g (0.01 mole) of dibutyltin sulfide and 6.33 g (0.01 mole) of bis(dibutylchlorotin)phosphate prepared as described in the foregoing Example 2 was heated at a temperature of 70° C. until a clear solution was obtained. A 17.96 g (0.12 mole) portion of 2-ethylhexanoic acid was added to this solution and the resultant mixture was heated at 70° C. for several minutes to obtain a clear liquid. This liquid was then combined with 35.92 g of dipropylene glycol and subsequently evaluated as a gel catalyst for a flexible polyurethane foam.

EXAMPLE 15

This example demonstrates the preparation of a reaction product of bis(dibutylchlorotin)phosphate, dibutyltin oxide and 2-ethylhexanoic acid.

A mixture containing 6.33 g (0.01 mole) of bis(dibutylchlorotin)phosphate, 12.45 g (0.05 mole) of dibutyltin oxide and 50 cc of toluene was heated under a nitrogen atmosphere using an oil bath. All of the solid material present dissolved to form a clear solution when the temperature of the oil bath reached 130° C. This solution was then concentrated by evaporation under reduced pressure to yield an amber-colored gel. One possible structure for this gel is

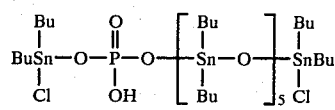

wherein Bu represents n—$C_4H_9$—. The gel was combined with 37.56 g (0.26 mole) of 2-ethylhexanoic acid and 75.12 g of dipropylene glycol. The resultant mixture was heated for 15 minutes at a temperature of 100° C. until the gel dissolved. The solution weighed 124 g.

EXAMPLE 16

Preparation of a reaction product of dibutyltin oxide, dibutyltin dichloride, phosphoric acid and 2-ethylhexanoic acid A reactor was filled with nitrogen and charged with 670 g (4.6 moles) of 2-ethylhexanoic acid and 124.4 g (0.5 mole) of dibutyltin oxide. This mixture was heated at 50°-55° C. with stirring until a clear solution was obtained. The 8 g of water which formed as a by-product of this reaction were removed by heating the reaction mixture to 100° C. under a pressure of 25-30 mm of mercury. The solution was then allowed to cool to 65°-70° C., at which time 152 g (0.50 mole) of dibutyltin dichloride was added and the reaction mixture was heated at a temperature of 60° C. for ½ an hour. A 58 g (0.5 mole) portion of phosphoric acid (as an 85% aqueous solution) was gradually added to the reactor. Following completion of the addition the reaction mixture was heated at 60° C. for one hour. A 5 g portion of a filtration aid was added and the reaction mixture was filtered to remove solid materials. The resultant solution was found to contain 11.96% tin, 3.41% phosphorus and 1.55% chlorine. The calculated values for the expected reaction product are 12.5% tin, 3.75% phosphorus and 1.65% chlorine.

EXAMPLE 17

Reaction product of bis(dibutylchlorotin)oxide and phenyl phosphonic acid

A reactor was charged with 55.3 g (0.1 mole) of bis(dibutylchlorotin)oxide, 14.2 g (0.09 mole) of phenyl phosphonic acid and 250 cc toluene. This mixture was heated at the boiling point for one hour during which time the 3.5 cc of water produced as a by-product of the reaction was collected in a Dean-Stark receiver. The resultant clear amber-colored solution was dried using a molecular sieve, after which the solvent and other volatile materials were removed by evaporation under reduced pressure. The resultant solid weighed 63.5 g (equivalent to 89% of the theoretical yield) and was found to contain 33.35% tin and 9.71% chlorine. The calculated values for the expected product are 33.49% tin and 10.0% chlorine.

EXAMPLE 18

The reaction products prepared using the procedures described in the foregoing Examples 13, 14, 15 and 16 were evaluated as gel catalysts in a flexible polyurethane foam formulation of the following composition:

| Ingredient | Parts by weight |
|---|---|
| Polyol¹ | 200 |

-continued

| Ingredient | Parts by weight |
| --- | --- |
| Water | 7.0 |
| Surfactant[2] | 2.0 |
| Triethylene diamine[3] | 0.6 |
| N-Ethyl morpholine | 0.6 |
| Toluene diisocyanate[4] | 90.6 |

[1] An ethylene oxide-propylene oxide copolymer available as Niax ® 16-56 from the Union Carbide Corporation
[2] Poly(oxyethylene oxypropylene) siloxane
[3] As a 33% by weight solution in dipropylene glycol
[4] Isocyanate Index = 105

Flexible polyurethane foams were prepared and evaluated using the procedures described in the preceeding Example 10.

| Compound of Example | Catalyst Level[1] | Cream Time[2] | Rise Time[2] | Dry Heat Test | 90% Compression Set (%) |
| --- | --- | --- | --- | --- | --- |
| 13 | 0.2 | 59 | 113 | pass | 6.89 |
| 14 | 0.2 | 65 | 125 | pass | 6.4 |
| 15 | 0.2 | 61 | 117 | pass | 6.04 |
| 16 | 0.2 | 65 | 131 | pass | 5.79 |
| stannous octoate* | 0.3 | 53 | 94 | pass | 5.69 |

*control
[1] expressed as parts by weight per 100 parts of polyol
[2] in seconds

EXAMPLE 19

This example discloses preparation of a flexible polyurethane foam using a catalyst composition of this invention wherein halogen and phosphorus are present in two different organotin compounds.

Dibutyltin hydrogen phosphate was prepared by charging a reactor with 105.3 g. (0.3 mole) of dibutyltin diacetate and 500 cc. toluene. A 34.5 g. portion of 85% aqueous phosphoric acid (0.3 mole $H_3PO_4$) was then added in a dropwise manner to the stirred reaction mixture. Stirring was continued for 30 minutes following completion of the addition. The reactor was then equipped with a watercooled condenser and the contents of the reactor were heated at the boiling point for about one hour. The liquid in the reactor was discarded and the remaining solid was dried under reduced pressure to yield 95.9 g. of a hard, colorless material (95% of theoretical yield). The solid was found to contain 34.79% tin and 9.61% phosphorus. The calculated values for the expected product, dibutyltin hydrogen phosphate, are 36.1% tin and 9.42% phosphorus.

A catalyst composition was prepared by dissolving 15 g. of dibutyltin hydrogen phosphate in 30 g. of tetrahydrofuran and 31.5 g. toluene. The vessel containing the resultant mixture was heated in hot water with stirring until the solid material dissolved. The solution was allowed to cool and then combined with 13.5 g. of dibutyltin dichloride. A clear solution formed when the mixture was stirred for a few minutes at ambient temperature.

A flexible polyurethane foam was prepared using the foregoing catalyst composition at a concentration of 0.2 parts per 100 parts of polyol and the following formulation:

| | Parts |
| --- | --- |
| Polyether polyol (hydroxyl No. = 57.6, avg. molecular wt.-3000) | 100 |

-continued

| | Parts |
| --- | --- |
| Water | 4 |
| Triethylene diamine (as 33% solution in propylene glycol) | 0.36 |
| Silicone type surfactant | 1.0 |
| Catalyst | 0.2 |
| Toluene diisocyanate | 50.1 |

A flexible polyurethane foam was prepared using a foam machine (Martin-Sweets Modern Module III). The reactants were metered into a square container measuring 14 inches (35 cm.) along each side and 7 inches (18 cm.) in depth. The foam required 86 seconds to rise to full height and did not exhibit any splits or voids. The final foam passed the dry heat test and had a 90% compression set value of 7%, which is within acceptable limits.

What is claimed is:

1. In a method for preparing flexible urethane foams by reacting a polyether polyol with an isocyanate in the presence of a gel catalyst and a blowing agent, the improvement therein which comprises using a gel catalyst composition comprising
 (a) a halogenated mono- or diorganotin ester of a phosphorus compound, or
 (b) a halogenated mono- or diorganotin compound and an organotin ester of a phosphorus compound, where halogen in (a) is bonded to tin or phosphorus and halogen in (b) is bonded to tin, and the phosphorus compound in (a) and (b) is selected from the group consisting of monomeric and condensed phosphoric acids, thiophosphoric, phosphorous, phosphinic, phosphinous, phosphonous and phosphonic acids, phosphoryl chloride and oligomeric condensation products of (1) phosphonic acid, (2) mixtures containing phosphoric and phosphonic acids or (3) esters of phosphoric and phosphorous acids and alcohols containing from 1 to 20 carbon atoms, and wherein the tin in said organotin compounds is in the tetravalent state, said foam having improved resiliency and heat stability.

2. A method according to claim 1 wherein the catalyst composition comprises a halogenated organotin ester of a phosphorus compound.

3. A method according to claim 2 wherein said phosphorus compound is selected from the group consisting of ortho-phosphoric acid, phenyl phosphonic acid, phosphoryl chloride and esters of phosphoric and phosphorous acids.

4. A method according to claim 2 wherein said organotin ester exhibits the general formula

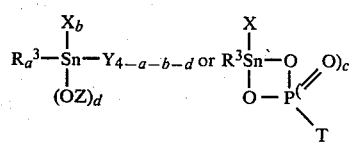

wherein X represents halogen, —OH, —OOCR[4], —OR[4] or —SR[5] wherein R[4] is hydrocarbyl and R[5] is hydrocarbyl, —R[6]COOR[4] or —R[6]OOCR[4] wherein R[4] is as defined above and R[6] is alkylene and contains from 2 to 20 carbon atoms; T is halogen or —OR[9]; Y is

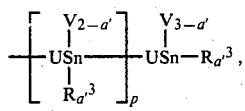

wherein V is —OZ or —X and X is as defined above;

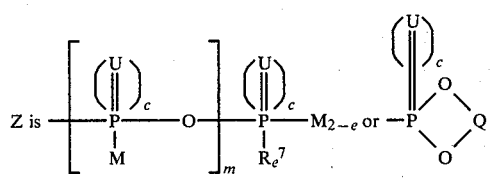

wherein $R^7$ is hydrocarbyl, chloroalkyl, halogen, —OH or —Y', M is —$R^8$, —$OR^9$, —$(OR^{10})_fOZ'$ or —Y', $R^8$ is hydrocarbyl, $R^9$ is hydrocarbyl or hydrogen, $R^{10}$ is —$CH_2CH_2$— or —$CH(CH_3)CH_2$—; Y' is

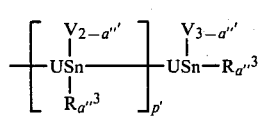

wherein V' is —OZ' or —X, X being defined above;

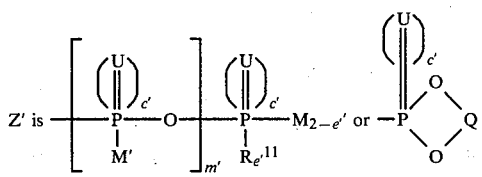

$R^{11}$ is hydrocarbyl, chloroalkyl, halogen or —OH, M' is $R^8$ or —$OR^9$, $R^8$ and $R^9$ are as defined above; U is an oxygen or sulfur atom; $R^3$ is hydrocarbyl or $R^{12}OOCR^{10}$—, wherein $R^{10}$ is as defined above and $R^{12}$ is hydrocarbyl, and Q is

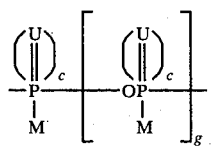

wherein U and M are as defined above; a is 1 or 2; a' is 1 or 2; a" is 1 or 2; b is 0, 1 or 2 with the proviso that b can only be 0 when the group represented by Y contains a halogen atom bonded to tin or phosphorus; c is 0 or 1; c' is 0 or 1; d is 0, 1 or 2 with the proviso that d can only be 0 when the group represented by Y contains phosphorus; e is 0, 1 or 2; e' is 0, 1 or 2; f is an integer from 1 to 100; g is 0 or an integer from 1 to 6; m is 0 or an integer from 1 to 10; m' is 0 or an integer from 1 to 10; p is 0 or an integer from 1 to 10; and p' is 0 or an integer from 1 to 10.

5. A method according to claim 4 wherein $R^3$ is alkyl or $R^{12}OOCR^{10}$— wherein $R^{12}$ is lower alkyl, $R^{10}$ is —$CH_2CH_2$—, X is halogen, a is 2, b is 1, d is 1, m is 0, e is 0, M is —$R^8$, —$OR^9$ or Y' and p' is 0 when M is Y'.

6. A method according to claim 4 wherein $R^3$ and $R^4$ are alkyl, M is alkyl or alkoxy and d is 0.

7. A method according to claim 6 wherein $R^3$ and $R^4$ are lower alkyl and M is lower alkoxy.

8. A method according to claim 4 where c is 1.

9. A method according to claim 4 where $R^3$ and $R^4$ are butyl, M is hydroxyl, b is 2, c is 1 and d is 0.

10. A method according to claim 4 wherein said organotin ester has the formula

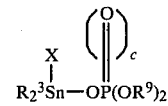

wherein $R^3$ is alkyl or $R^{12}OOCCH_2CH_2$—, $R^9$ and $R^{12}$ are alkyl and X is halogen.

11. A method according to claim 10 wherein $R^3$ and $R^9$ are lower alkyl containing from 1 to 4 carbon atoms.

12. A method according to claim 4 wherein said organotin ester has the formula

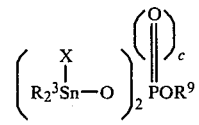

wherein $R^3$ is alkyl or $R^{12}OOCCH_2CH_2$—, $R^9$ and $R^{12}$ are alkyl and X is halogen.

13. A method according to claim 4 wherein said organotin ester has the formula

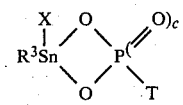

wherein $R^3$ is alkyl, X is halogen and T is halogen or alkoxy containing from 1 to 8 carbon atoms.

14. A method according to claim 1 wherein the catalyst composition comprises (1) a halogenated organotin compound of the general formula $R_a{}^3SnX_{4-a}$, where $R^3$ is hydrocarbyl or $R^5OOCR^6$— and X is halogen and (2) an organotin ester of a phosphorus compound, the organotin ester having the general formula

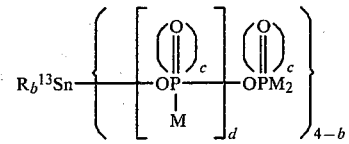

where $R^{13}$ is hydrocarbyl or $R^{14}OOCR^{15}$— where $R^5$ is hydrocarbyl, $R^6$ is —$CH_2CH(CH_3)$— or —$CH_2CH_2$—, and $R^{14}$ and $R^{15}$ are selected from the group as $R^5$ and $R^6$, respectively; M is hydrocarbyl or —$OR^7$, wherein $R^7$ is hydrogen or hydrocarbyl, b is 1 or 2, c is 0 or 1 and d is 0 or an integer from 1 to 6.

15. A method according to claim 14 wherein $R^3$ and $R^4$ are identical or different alkyl, M is hydroxyl, b is 2, c is 1 and d is 0.

16. A method according to claim 15 wherein $R^3$ and $R^4$ are lower alkyl.

17. A method according to claim 14 wherein X is chlorine.

18. A method according to claim 14 wherein the molar ratio of tin to phosphorus in said composition is from 0.045 to 23, the molar ratio of tin to halogen is from 0.5 to 23 and the molar ratio of phosphorus to halogen is from 0.5 to 22.

19. A method according to claim 1 wherein said catalyst composition additionally comprises a mono- or dicarboxylic acid containing from 2 to 20 carbon atoms.

20. A method according to claim 19 wherein said acid constitutes from 10 to 90% by weight of said catalyst composition.

21. A method according to claim 19 wherein said acid contains from 4 to 12 carbon atoms.

22. A method according to claim 21 wherein said acid contains 8 carbon atoms.

23. A composition comprising
 (a) a mono- or dicarboxylic acid containing from 2 to 20 carbon atoms and
 (b) a halogenated mono- or diorganotin ester of a phosphorus compound selected from the group consisting of monomeric acid condensed phosphoric acids, thiophosphoric, phosphorous, phosphinic, phosphinous, phosphonous and phosphonic acid, phosphoryl chloride and oligomeric condensation products of (1) phosphonic acid, (2) mixtures containing phosphonic and phosphonous acids or (3) esters of phosphoric and phosphorous acids and alcohols containing from 1 to 20 carbon atoms, and wherein the tin in organotin ester is in the tetravalent state.

24. A composition according to claim 23 wherein said phosphorus compound is selected from the group consisting of ortho-phosphoric acid, phenyl phosphonic acid, phosphoryl chloride and esters of phosphoric and phosphorous acids.

25. A composition according to claim 23 wherein said organotin ester exhibits the general formula

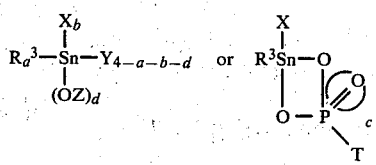

wherein X represents halogen, —OH, —OOCR$^4$, —OR$^4$ or —SR$^5$ wherein R$^4$ is hydrocarbyl and R$^5$ is hydrocarbyl, —R$^6$COOR$^4$ or —R$^6$OOCR$^4$ wherein R$^4$ is as defined above and R$^6$ is alkylene and contains from 2 to 20 carbon atoms; T is halogen or —OR$^9$; Y is

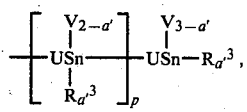

wherein V is —OZ or —X and X is as defined above;

Z is 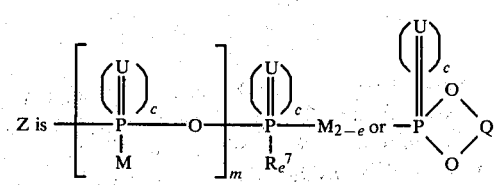

wherein R$^7$ is hydrocarbyl, chloroalkyl, halogen, —OH or —Y', M is —R$^8$, —OR$^9$, —(OR$^{10}$)$_f$OZ' or —Y', R$^8$ is hydrocarbyl, R$^9$ is hydrocarbyl or hydrogen, R$^{10}$ is —CH$_2$CH$_2$— or —CH(CH$_3$)CH$_2$—; Y' is

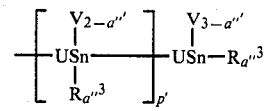

wherein V' is —OZ' or —X, X being defined above; Z' is

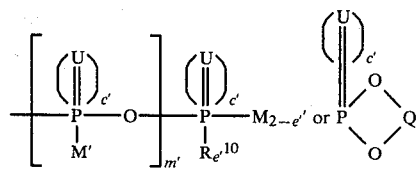

R$^{11}$ is hydrocarbyl, chloroalkyl, halogen or —OH, M' is R$^8$ or —OR$^9$, R$^8$ and R$^9$ are as defined above; U is an oxygen or sulfur atom; R$^3$ is hydrocarbyl or R$^{12}$OOCR$^{10}$—, wherein R$^{10}$ is as defined above and R$^{12}$ is hydrocarbyl, and Q is

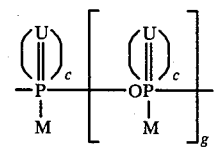

wherein U and M are as defined above; a is 1 or 2; a' is 1 or 2; a'' is 1 or 2; b is 0, 1 or 2 with the proviso that b can only be 0 when the group represented by Y contains a halogen atom bonded to tin or phosphorus; c is 0 or 1; c' is 0 or 1; d is 0, 1 or 2 with the proviso that d can only be 0 when the group represented by Y contains phosphorus; e is 0, 1 or 2; e' is 0, 1 or 2; f is an integer from 1 to 100; g is 0 or an integer from 1 to 6; m is 0 or an integer from 1 to 10; m' is 0 or an integer from 1 to 10; p is 0 or an integer from 1 to 10; and p' is 0 or an integer from 1 to 10.

26. A composition according to claim 25 wherein R$^3$ is alkyl or R$^{12}$OOCR$^{10}$—, wherein R$^{12}$ is lower alkyl, R$^{10}$ is —CH$_2$CH$_2$—, X is halogen, a is 2, b is 1, d is 1, m is 0, e is 0, M is —R$^8$, —OR$^9$ or Y' and p' is 0 when M is Y'.

27. A composition according to claim 25 where R$^3$ and R$^4$ are alkyl, M is alkyl or alkoxy and d is 0.

28. A composition according to claim 27 wherein R$^3$ and R$^4$ are lower alkyl and M is lower alkoxy.

29. A composition according to claim 25 where c is 1.

30. A composition according to claim 25 where R$^3$ and R$^4$ are butyl, M is hydroxyl, b is 2, c is 1 and d is 0.

31. A composition according to claim 25 wherein said organotin ester has the formula

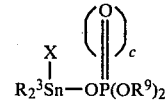

wherein $R^3$ is alkyl or $R^{12}OOCCH_2CH_2-$, $R^9$ and $R^{12}$ are alkyl and X is halogen.

32. A composition according to claim 31 wherein $R^3$ and $R^9$ are lower alkyl containing from 1 to 4 carbon atoms.

33. A composition according to claim 25 wherein said organotin ester has the formula

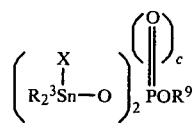

wherein $R^3$ is alkyl or $R^{12}OOCCH_2CH_2-$, $R^9$ and $R^{12}$ are alkyl and X is halogen.

34. A composition according to claim 25 wherein said organotin ester has the formula

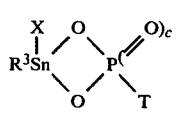

wherein $R^3$ is alkyl, X is halogen and T is halogen or alkoxy containing from 1 to 8 carbon atoms.

35. A composition comprising (1) a halogenated organotin compound of the general formula $R_a{}^3SnX_{4-a}$ where $R^3$ is hydrocarbyl or $R^5OOCR^6-$ and X is halogen and (2) an organotin ester of a phosphorus compound, the organotin ester having the general formula

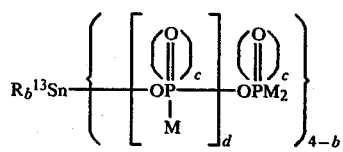

where $R^{13}$ is hydrocarbyl or $R^{14}OOCR^{15}-$ where $R^5$ is hydrocarbyl, $R^6$ is $-CH_2CH(CH_3)-$ or $-CH_2CH_2-$, $R^{14}$ and $R^{15}$ are selected from the same group as $R^5$ and $R^6$, respectively, M is hydrocarbyl or $-OR^7$, wherein $R^7$ is hydrogen or hydrocarbyl, b is 1 or 2, c is 0 or 1 and d is 0 or an integer from 1 to 6.

36. A composition according to claim 35 wherein $R^3$ and $R^4$ are identical or different alkyl, M is hydroxyl, b is 2, c is 1 and d is 0.

37. A compound according to claim 36 wherein $R^3$ and $R^4$ are lower alkyl.

38. A composition according to claim 35 wherein X is chlorine.

39. A composition according to claim 35 wherein the molar ratio of tin to phosphorus is from 0.045 to 23, the molar ratio of tin to halogen is from 0.5 to 23 and the molar ratio of phosphorus to halogen is from 0.5 to 22.

40. In a curable, foamable composition comprising
(a) a polyol,
(b) a polyfunctional isocyanate,
(c) a blowing agent and
(d) a gel catalyst,
the improvement wherein the gel catalyst comprises a halogenated mono- or diorganotin ester of phosphoric acid, phosphorous acid, phosphonic acid, phosphinic acid or phosphoryl chloride, wherein the halogen is chlorine, bromine or iodine.

41. A composition according to claim 40 wherein the catalyst contains
from 3 to 30% by weight of tin,
from 2 to 30% by weight of phosphorus and
from 3 to 30% by weight of said halogen.

42. A composition according to claim 40 wherein the catalyst exhibits the formula

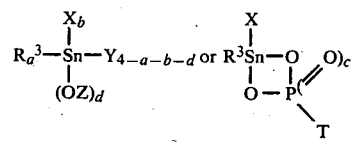

wherein X represents halogen, $-OH$, $-OOCR^4$, $-OR^4$ or $-SR^5$, wherein $R^4$ is hydrocarbyl and $R^5$ is hydrocarbyl, $-R^6COOR^4$ or $-R^6OOCR^4$ wherein $R^4$ is as defined above and $R^6$ is alkylene and contains from 2 to 20 carbon atoms; T is halogen or $-OR^9$; Y is

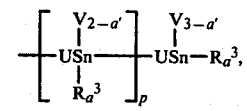

wherein V is $-OZ$ or $-X$ and X is as defined above; Z is

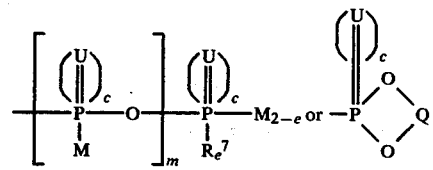

wherein $R^7$ is hydrocarbyl chloroalkyl, halogen, $-OH$ or $-Y'$, M is $-R^8$, $-OR^9$, $-(OR^{10})/OZ'$ or $-Y'$, $R^8$ is hydrocarbyl, $R^9$ is hydrocarbyl or hydrogen, $R^{10}$ is $-CH_2CH_2-$ or $-CH(CH_3)CH_2-$; Y' is

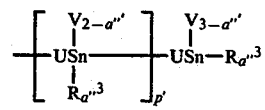

wherein V' is $-OZ'$ or $-X$, X being defined above; Z' is

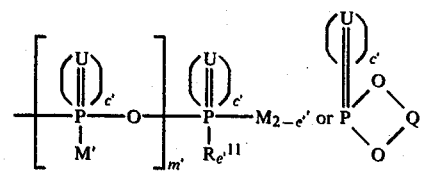

$R^{11}$ is hydrocarbyl, chloroalkyl, halogen or $-OH$, M' is $R^8$ or $-OR^9$, $R^8$ and $R^9$ are as defined above; U is an oxygen or sulfur atom; $R^3$ is hydrocarbyl or $R^{12}OOCR^{10}-$, wherein $R^{10}$ is as defined above and $R^{12}$ is hydrocarbyl, and Q is

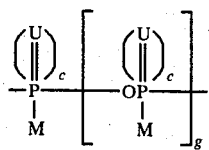

wherein U and M are as defined above; a is 1 or 2; a' is 1 or 2; a'' is 1 or 2; b is 0, 1 or 2 with the proviso that b can only be 0 when the group represented by Y contains a halogen atom bonded to tin or phosphorus; c is 0 or 1; c' is 0 or 1; d is 0, 1 or 2 with the proviso that d can only be 0 when the group represented by Y contains phosphorus; e is 0, 1 or 2; e' is 0, 1 or 2; f is an integer from 1 to 100; g is 0 or an integer from 1 to 6; m is 0 or an integer from 1 to 10; m' is 0 or an integer from 1 to 10; p is 0 or an integer from 1 to 10; and p' is 0 or an integer from 1 to 10.

43. A composition according to claim 40 wherein the catalyst exhibits the general formula

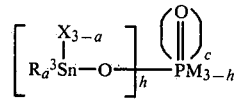

wherein
R$^3$ is alkyl, cycloalkyl, phenylalkyl or alkylphenyl, wherein any alkyl group or the alkyl portion of any phenylalkyl or alkylphenyl group contains from 1 to 20 carbon atoms, or R$^3$ is R$^{12}$OOCR$^{10}$— wherein R$^{10}$ is —CH(CH$_3$)CH$_2$— and R$^{12}$ is alkyl and contains from 1 to 20 carbon atoms, M is selected from the same group as R$^3$ or is —OR$^9$ wherein R$^9$ is hydrogen or is alkyl, cycloalkyl, phenyl, alkylphenyl or phenylalkyl, wherein any alkyl group or the alkyl portion of any alkylphenyl or phenyl alkyl group contains from 1 to 20 carbon atoms.

X is chlorine, bromine or iodine,
a is 0 or 1 and
h is 1 or 2.

44. A composition according to claim 43 wherein R$^3$ is alkyl and contains from 1 to 4 carbon atoms, X is chlorine and M is phenyl or —OR$^9$ wherein R$^9$ is hydrogen or alkyl containing from 1 to 4 carbon atoms.

45. A composition according to claim 40 wherein the concentration of gel catalyst is from 0.01 to 10%, based on the weight of polyol.

46. A composition according to claim 45 wherein the gel catalyst concentration is from 0.1 to 1%, based on the weight of polyol.

* * * * *